(12) United States Patent
Jenkins et al.

(10) Patent No.: US 6,599,129 B2
(45) Date of Patent: Jul. 29, 2003

(54) METHOD FOR ADAPTIVE TRAINING OF SHORT TERM MEMORY AND AUDITORY/VISUAL DISCRIMINATION WITHIN A COMPUTER GAME

(75) Inventors: William M. Jenkins, Pacifica, CA (US); Michael M. Merzenich, San Francisco, CA (US); Steven L. Miller, Pacifica, CA (US); Bret E. Peterson, Lafayette, CA (US); Paula Tallal, Lumberville, PA (US)

(73) Assignee: Scientific Learning Corporation, Oakland, CA (US)

( * ) Notice: Subject to any disclaimer, the term of this patent is extended or adjusted under 35 U.S.C. 154(b) by 118 days.

(21) Appl. No.: 09/961,554

(22) Filed: Sep. 24, 2001

(65) Prior Publication Data

US 2002/0034717 A1 Mar. 21, 2002

Related U.S. Application Data

(60) Division of application No. 09/106,939, filed on Jun. 30, 1998, now Pat. No. 6,331,115, which is a continuation-in-part of application No. 09/982,189, filed on Dec. 17, 1997, now Pat. No. 5,927,988.

(51) Int. Cl.[7] .................................................. G09B 5/00
(52) U.S. Cl. ....................... 434/169; 434/167; 434/185; 434/307 R; 704/254; 463/17; 345/716
(58) Field of Search ................................ 434/118, 156, 434/157, 169, 178, 185, 307 R, 308, 322, 323, 362, 365; 709/927; 704/254, 270, 503, 504; 345/716; 463/9, 17, 20, 29, 40, 43; 273/237, 271, 431, 460; 84/477 R, 610, 611

(56) References Cited

U.S. PATENT DOCUMENTS

| | | | |
|---|---|---|---|
| 3,920,903 A | | 11/1975 | Beller |
| 4,569,026 A | | 2/1986 | Best |
| 4,884,972 A | | 12/1989 | Gasper |
| 4,907,274 A | | 3/1990 | Nomura et al. |
| 5,170,432 A | | 12/1992 | Hackbarth et al. |
| 5,175,794 A | | 12/1992 | Tattersall |
| 5,231,568 A | * | 7/1993 | Cohen et al. .................. 463/17 |
| 5,336,093 A | | 8/1994 | Cox |
| 5,429,513 A | | 7/1995 | Diaz-Plaza |
| 5,640,490 A | | 6/1997 | Hansen et al. |
| 5,799,267 A | | 8/1998 | Siegel |
| 5,813,862 A | | 9/1998 | Merzenich et al. |
| 5,855,513 A | * | 1/1999 | Lam .............................. 463/9 |
| 5,860,064 A | | 1/1999 | Henton |
| 5,868,683 A | | 2/1999 | Protopapas et al. |
| 5,873,061 A | | 2/1999 | Häb-Umbach et al. |
| 5,916,024 A | * | 6/1999 | Von Kohorn ................. 463/40 |
| 6,019,607 A | * | 2/2000 | Jenkin et al. ................ 434/116 |
| 6,026,361 A | | 2/2000 | Hura |
| 6,036,496 A | | 3/2000 | Miller et al. |
| 6,071,123 A | | 6/2000 | Tallal et al. |
| 6,076,060 A | | 6/2000 | Lin et al. |
| 6,078,885 A | | 6/2000 | Beutnagel |
| 6,094,633 A | | 7/2000 | Gaved et al. |
| 6,099,318 A | * | 8/2000 | McLeod et al. ............. 434/129 |
| 6,109,107 A | | 8/2000 | Wright et al. |
| 6,113,645 A | | 9/2000 | Bentiz et al. |
| 6,177,623 B1 | * | 1/2001 | Ooseki ....................... 84/477 R |
| 6,347,996 B1 | * | 2/2002 | Gilmore et al. ............... 463/17 |

* cited by examiner

Primary Examiner—Joe H. Cheng
(74) Attorney, Agent, or Firm—James W. Huffman

(57) ABSTRACT

A method for training of auditory and graphical discrimination in humans, and a human's short term memory, is provided within an animated game environment. The method provides a number of stimulus sets, each stimulus set having similar sounding phonemes associated with graphemes. Upon initiation of a trial, a grid of tiles is presented to a subject. The subject selects the tiles, one at a time. As the tiles are selected, an associated phoneme is presented to the subject. The subject clears away tiles by pairing them with identical tiles. When all the tiles in a trial are cleared, the subject is either promoted or demoted in skill level. Promotion/demotion varies the number of tiles presented, the phonemes used within each trial, and the amount of audio processing that is applied to the phonemes.

7 Claims, 10 Drawing Sheets

METHOD FOR ADAPTIVE TRAINING OF SHORT TERM MEMORY AND AUDITORY/VISUAL DISCRIMINATION WITHIN A COMPUTER GAME

CROSS REFERENCE TO RELATED APPLICATIONS

This application is a Divisional of U.S. patent application Ser. No. 09/106,939, filed on Jun. 30, 1998, now U.S. Pat. No. 6,331,115 B1, entitled "METHOD FOR ADAPTIVE TRAINING OF SHORT TERM MEMORY AND AUDITORY/VISUAL DISCRIMINATION WITHIN A COMPUTER GAME", which is a Continuation-In-Part of U.S. application Ser. No. 08/982,189, filed on Dec. 17, 1997, now U.S. Pat. No. 5,927,988, entitled "METHOD AND APPARATUS FOR TRAINING OF SENSORY AM) PERCEPTUAL SYSTEMS IN LLI SUBJECTS"; and is related to U.S. Pat. No. 6,019,607, entitled "METHOD AND APPARATUS FOR TRAINING OF SENSORY AND PERCEPTUAL SYSTEMS IN LLI SUBJECTS"; and U.S. Pat. No. 6,159,014, entitled "METHOD AND APPARATUYS FOR TRAINING COGNITIVE AND MEMORY SYSTEMS IN HUMAN"; all assigned to Scientific Learning Corporation, and all of which are incorporated herein by reference.

BACKGROUND OF THE INVENTION

1. Field of the Invention

This invention relates in general to the field of language education, and more specifically to a computer program for training a human's auditory processing system to discriminate between and accurately identify similarly sounding phonemes or words, and to associate representative graphemes with the phonemes or words.

2. Description of the Related Art

Up to ten percent of children have language-learning impairments (LLI) resulting from the inability to accurately process short duration acoustic events at the rates that occur in normal speech. Their trouble distinguishing among elements of speech is neurologically based and has far reaching consequences, including: academic failure, emotional and disciplinary problems, and possibly diminished lifelong achievement and self-image. No bracket of intelligence, race, gender or economic level is immune from this problem.

More specifically, Children with LLI have difficulty detecting and identifying sounds that occur simultaneously or in close proximity to each other—a phenomenon known as "masking." Because of masking, children with LLI require sounds that are as much as 45 decibels more intense than a preceding or subsequent masking noise to distinguish and understand them. In addition, children with LLI are consistently poorer at detecting a brief tone presented with a masking noise, particularly when the brief tone is turned on immediately prior to the masking noise. This phenomenon is called "backward masking." Similarly, when the brief tone is turned on immediately after the masking noise a similar decrease in detectability can occur. This phenomenon is called "forward masking". For a tone to be detected by a child with LLI in the presence of a masking noise, the tone must be separated in time or frequency from the masking noise.

The inability to accurately distinguish and process short duration sounds often causes children to fall behind in school. Since the children can't accurately interpret many language sounds, they can't remember which symbols represent which sounds. This deficiency causes difficulties in learning to read (translating from symbols to sounds), and in spelling. In fact, it is common for a child with LLI to fall two to three years behind his/her peers in speech, language and reading development.

One way children develop such auditory processing problems is from middle ear infections when they are young and beginning to develop the oral representations of language in the central auditory nervous system. When a child has an ear infection, fluid can build up and block or muffle the sound wave entering the ear causing intermittent hearing loss. Even if the infection doesn't permanently damage the ear, the child's brain doesn't learn to process some sounds because it hasn't heard them accurately before, on a consistent basis. This typically occurs during a critical period of brain development when the brain is building the nerve connections necessary to accurately process acoustic events associated with normal speech.

Researchers believe that the auditory processing problem is essentially one of timing. Vowel sounds like /a/ and /e/ usually last at least 100 milliseconds and typically have constant frequency content. Consonants, on the other hand, typically have modulated frequency components, and last less than 40 milliseconds. Children with LLI cannot process these faster speech elements, especially the hard consonants like /t/, /p/, /d/ and /b/, if they occur either immediately before or after vowels, or if they are located near other consonants. Rather than hearing the individual sounds that make up a particular phoneme, children with LLI integrate closely associated sounds together over time. Since the duration of vowels are typically longer than consonants, the modulated frequency portions of consonants are often lost in the integration, an affect that may also hinder the resolution of the vowel, particularly short duration vowels.

This problem of abnormal temporal integration of acoustic events over time is not limited to children with LLI. Rather, the problem extends to stroke victims who have lost the neurological connections necessary to process speech, as well as to individuals raised in one country, having one set of language phonemes, and attempting to learn the language of another country, having a distinct set of language phonemes. For example, it is known that an individual raised in Japan is not often presented with phonemes similar to the English r's and l's, because those consonants are not common in the Japanese language. Similarly, there are many subtleties in the sounds made by a speaker of Japanese that are difficult to distinguish unless raised in Japan. The phonetic differences between languages are distinctions that must be learned, and are often very difficult. But, they are clearly problems that relate to the temporal processing of short duration acoustic events.

The above described temporal processing deficiency has little if anything to do with intelligence. In fact, some LLI specialists argue that brains choosing this different route by which to absorb and reassemble bits of speech may actually stimulate creative intelligence, but at the expense of speech and reading problems.

Recent studies have shown that if the acoustic events associated with phonemes that are difficult to distinguish, such as /ba/ and /da/, are slowed down, or that the consonant portion of the phonemes are emphasized, that students diagnosed as LLI can accurately distinguish between the phonemes. In addition, if the interval between two complex sounds is lengthened, LLI students are better able to process the sounds distinctly.

Heretofore, the solution to the processing problem has been to place LLI students in extended special education and/or speech therapy training programs that focus on speech recognition and speech production. Or, more commonly, repetitive reading programs, phonic games, or other phonic programs are undertaken. These programs often last for years, with a success rate that is often more closely associated with the skill of the speech and language professional than with the program of study.

What is needed is a method and apparatus that allows a subject with abnormal temporal processing to train, or retrain their brain to recognize and distinguish short duration acoustic events that are common in speech. Moreover, what is needed is a program that repetitively trains a subject to distinguish phonemes at a normal rate, by emphasizing elements of speech to the point that they are distinguishable, and then adaptively adjusting the emphasis of the speech elements to the level of normal speech. The adaptive adjustments should be made so as to encourage the subject to continue with the repetitions, and the number of repetitions should be sufficient to develop the necessary neurological connections for normal temporal processing of speech. Moreover, the program should provide acoustic signals to the brain that are better for phonetic training than normal human speech.

Furthermore, what is needed is a program that trains a subject to discriminate between similar phonemes in increasingly complex situations (i.e., identifying sounds at the beginning, middle and end of words), to identify sequences of stimuli that are delivered in rapid succession (i.e., at speeds common in normal speech), and to begin associating phonemes with particular graphic representations (graphemes).

SUMMARY

To address the above-detailed deficiencies, the present invention provides a method for adaptively training a subject's working memory by presenting a plurality of tiles within a video game environment, the plurality of tiles playing a plurality of phonemes when selected, each of the plurality of tiles having at least one corresponding tile that plays the same auditory phoneme. The method includes: a) upon selection of a first one of the plurality of tiles, playing a first phoneme, and displaying the first phoneme's associated grapheme; b) upon selection of a second one of the plurality of tiles, playing a second phoneme; c) if the first and second phonemes are the same, and are selected sequentially, removing both the first and second one of the plurality of tiles; d) if the first and second phonemes are not the same, retaining both the first and second one of the plurality of tiles until they are selected sequentially.

DETAILED DESCRIPTION

Figure 1:
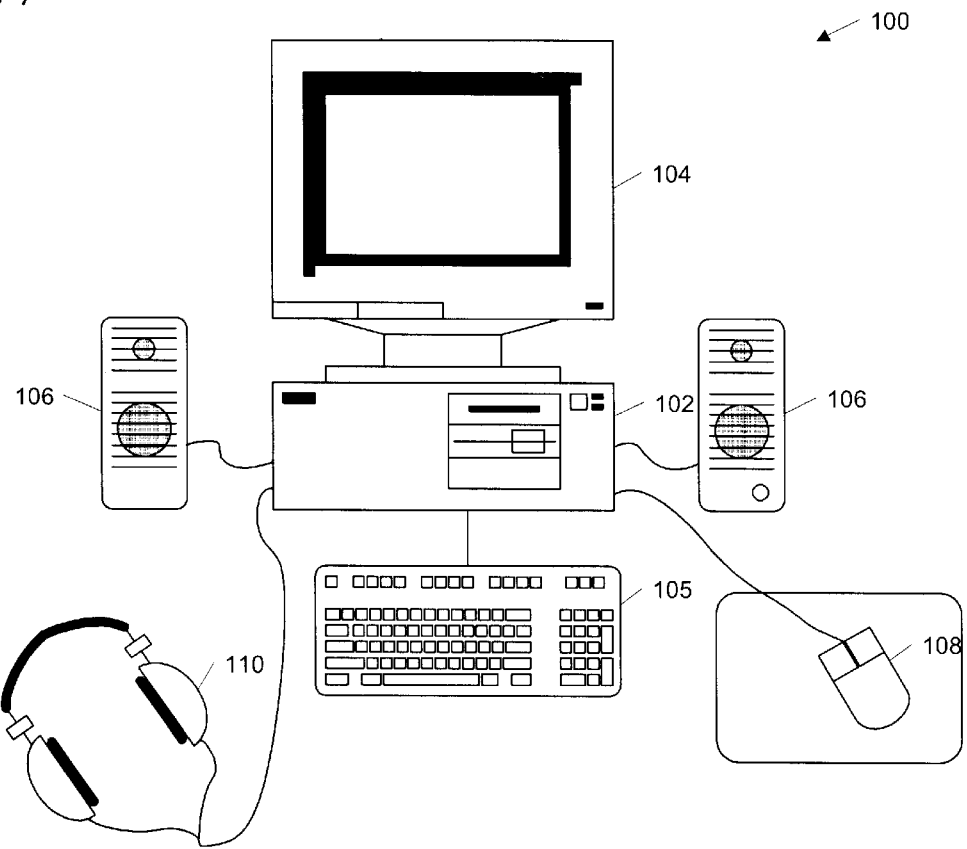
FIG. 1 is a block diagram of a computing system according to the present invention.

Referring to FIG. 1, a computer system 100 is shown for executing a computer program to train, or retrain a subject, according to the present invention. The computer system 100 contains a computer 102, having a CPU, memory, hard disk and CD ROM drive (not shown), attached to a monitor 104. The monitor 104 provides visual prompting and feedback to the subject during execution of the computer program. Attached to the computer 102 are a keyboard 105, speakers 106, a mouse 108, and headphones 110. The speakers 106 and the headphones 110 provide auditory prompting and feedback to the subject during execution of the computer program. The mouse 108 allows the subject to navigate through the computer program, and to select particular responses after visual or auditory prompting by the computer program. The keyboard 105 allows an instructor to enter alpha numeric information about the subject into the computer 102. Although a number of different computer platforms are applicable to the present invention, embodiments of the present invention execute on either IBM compatible computers or Macintosh computers.

Figure 2:
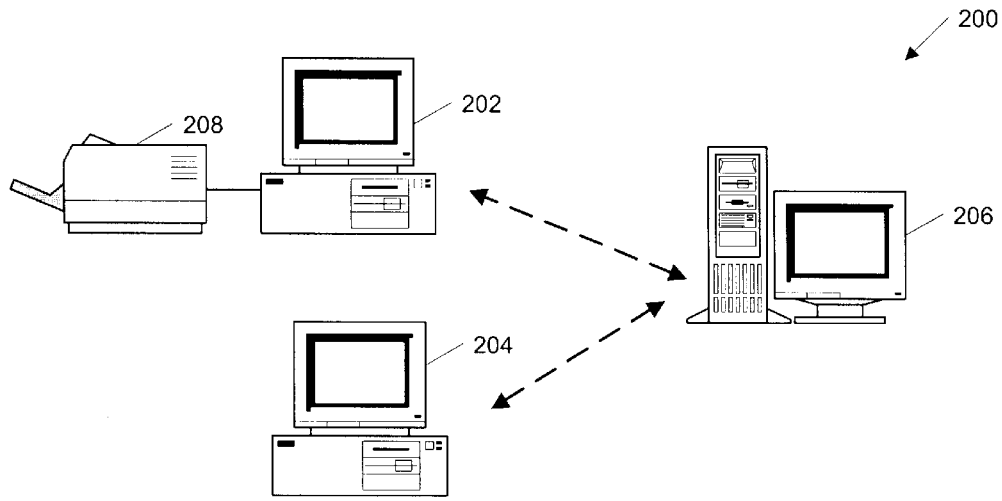
FIG. 2 is a block diagram of a networked computing system according to the present invention.

Now referring to FIG. 2, a computer network 200 is shown. The computer network 200 contains computers 202, 204, similar to that described above with reference to FIG. 1, connected to a server 206. The connection between the computers 202, 204 and the server 206 can be made via a local area network (LAN), a wide area network (WAN), or via modem connections, directly or through the Internet. A printer 208 is shown connected to the computer 202 to illustrate that a subject can print out reports associated with the computer program of the present invention. The computer network 200 allows information such as test scores, game statistics, and other subject information to flow from a subject's computer 202, 204 to a server 206. An administrator can then review the information and can then download configuration and control information pertaining to a particular subject, back to the subject's computer 202, 204.

Before providing a detailed description of the present invention, a brief overview of certain components of speech will be provided, along with an explanation of how these components are processed by LLI subjects. Following the overview, general information on speech processing will be provided so that the reader will better appreciate the novel aspects of the present invention.

Figure 3:
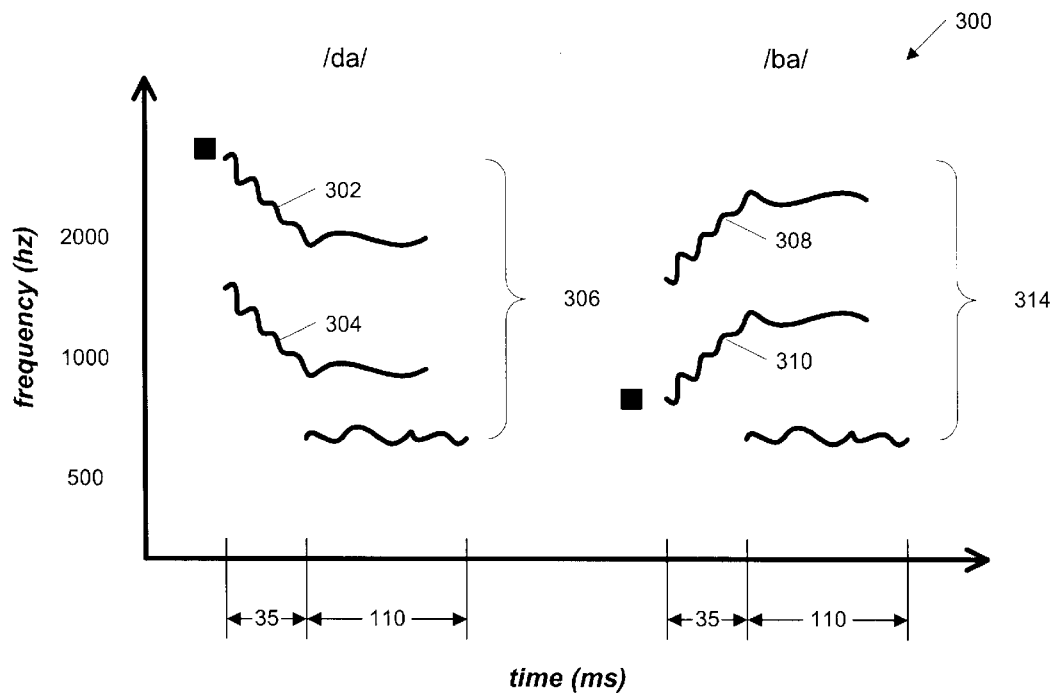
FIG. 3 is a chart illustrating frequency versus time of phonemes.

Referring to FIG. 3, a chart is shown that illustrates frequency components, over time, for two distinct phonemes within the English language. Although different phoneme combinations are applicable to illustrate features of the present invention, the phonemes /da/ and /ba/ are shown. For the phoneme /da/, a downward sweep frequency component 302, at approximately 2.5–2 khz is shown to occur over a 35 ms interval. In addition, a downward sweep frequency component 304, at approximately 1 khz is shown to occur during the same 35 ms interval. At the end of the 35 ms interval, constant frequency components 306 are shown, whose duration is approximately 110 ms. Thus, in producing the phoneme /da/, the stop consonant portion of the element /d/ is generated, having high frequency sweeps of short duration, followed by a long vowel element /a/ of constant frequency.

Also shown are frequency components for a phoneme /ba/. This phoneme contains an upward sweep frequency component 308, at approximately 2 khz, having a duration of approximately 35 ms. The phoneme also contains an upward sweep frequency component 310, at approximately 1 khz, during the same 35 ms period. Following the stop consonant portion /b/ of the phoneme, are constant frequency vowel portions 314 whose duration is approximately 110 ms.

Thus, both the /ba/ and /da/ phonemes begin with stop consonants having modulated frequency components of relatively short duration, followed by a constant frequency vowel components of longer duration. The distinction between the phonemes exists primarily in the 2 khz sweeps during the initial 35 ms interval. Similarity exists between other stop consonants such as /ta/, /pa/, /ka/ and /ga/.

Figure 4:
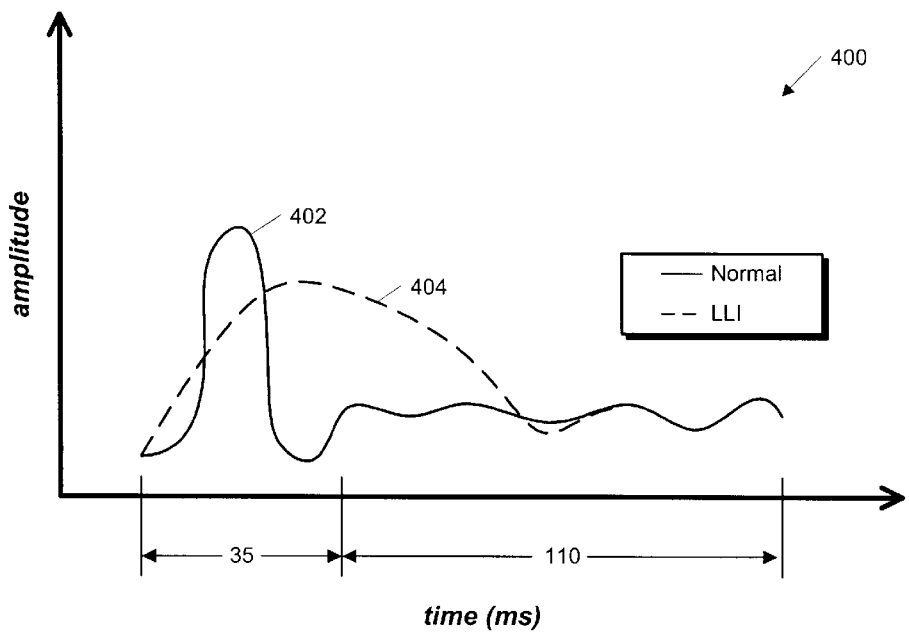
FIG. 4 is a chart illustrating a backward masking problem associated with Language Learning Impaired subjects.

Referring now to FIG. 4, the amplitude of a phoneme, for example /ba/, is viewed in the time domain. A short duration high amplitude peak waveform 402 is created upon release of either the lips or the tongue when speaking the consonant portion of the phoneme, that rapidly declines to a constant amplitude signal of longer duration. For an individual with normal temporal processing, the waveform 402 will be understood and processed essentially as it is. However, for an individual who is learning-language impaired, or who has abnormal temporal processing, the short duration, higher frequency consonant burst will be integrated over time with the lower frequency vowel, and depending on the degree of impairment, will be heard as the waveform 404. The result is that the information contained in the higher frequency sweeps associated with consonant differences, will be muddled, or indistinguishable.

With the above general background of speech elements, and how LLI subjects process them, a general overview of speech processing will now be provided. As mentioned above, one problem that exists in LLI subjects is the inability to distinguish between short duration acoustic events. If the duration of these acoustic events is stretched, in the time domain, it is possible to train LLI subjects to distinguish between these acoustic events. An example of such time domain stretching is shown in FIG. 5, to which attention is now directed.

Figure 5:
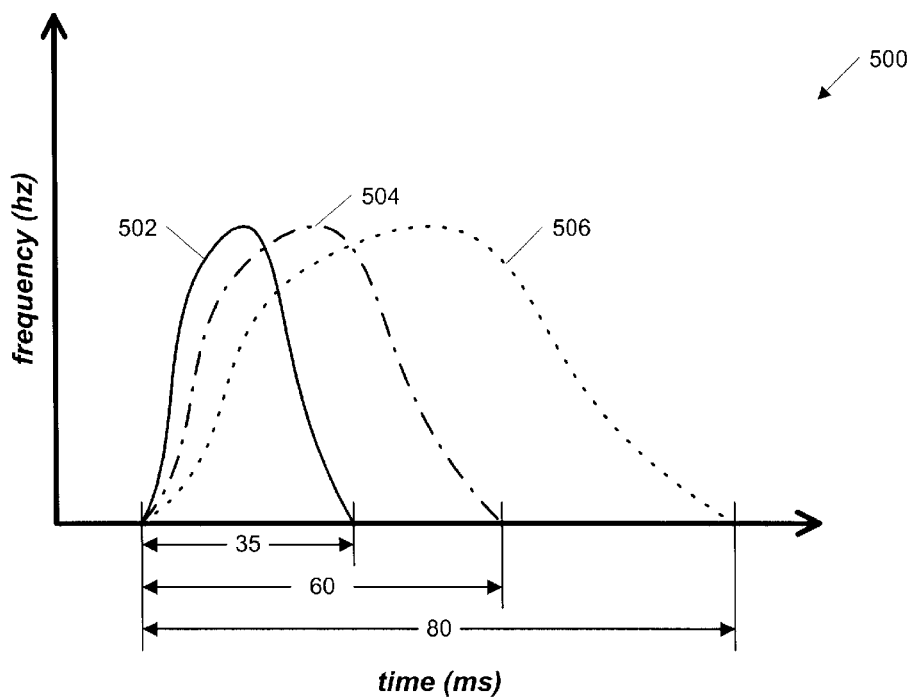
FIG. 5 is a chart illustrating frequency versus time duration.

In FIG. 5, a frequency vs. time graph 500 is shown that illustrates a waveform 502 having short duration characteristics similar to the waveform 402 described above. Using existing computer technology, the analog waveform 502 can be sampled and converted into digital values. The values can then be manipulated so as to stretch the waveform in the time domain to a predetermined length, while preserving the amplitude and frequency components of the modified waveform. The modified waveform can then be converted back into an analog waveform for reproduction by a computer, or by some other audio device. The waveform 502 is shown stretched in the time domain to durations of 60 ms (waveform 504), and 80 ms (waveform 506). By stretching the consonant portion of the waveform 502 without effecting its frequency components, subjects with LLI can begin to hear distinctions in common phonemes.

Figure 6:
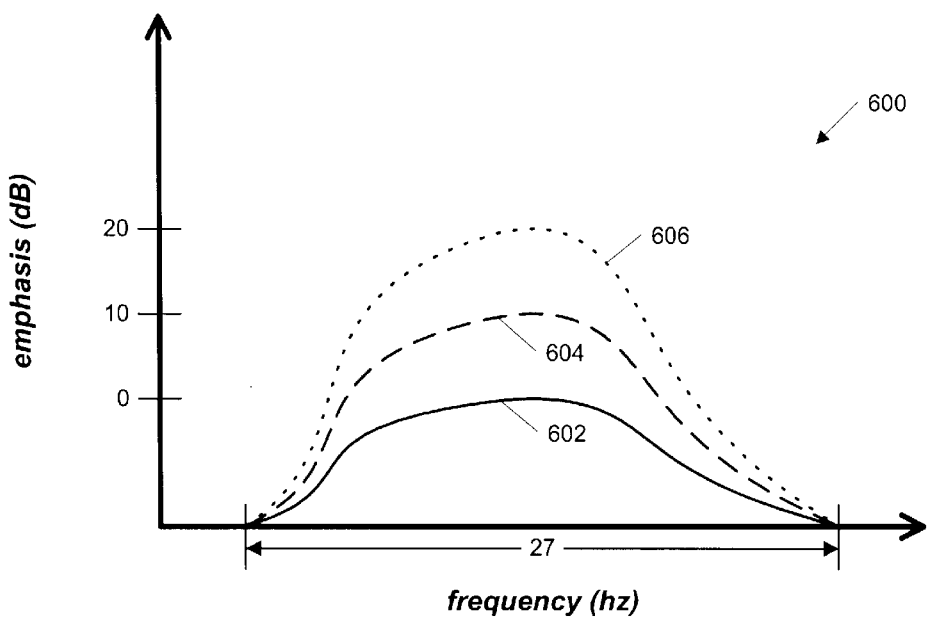
FIG. 6 is a chart illustrating amplitude emphasis of particular frequencies.

Another method that may be used to help LLI subjects distinguish between phonemes is to emphasize selected frequency envelopes within a phoneme. Referring to FIG. 6, a graph 600 is shown illustrating a frequency envelope 602 whose envelope varies by approximately 27 hz. By detecting frequency modulated envelopes that vary from say 3–30 hz, similar to frequency variations in the consonant portion of phonemes, and selectively emphasizing those envelopes, they are made more easily detectable by LLI subjects. A 10 dB emphasis of the envelope 602 is shown in waveform 604, and a 20 dB emphasis in the waveform 606.

Figure 7:
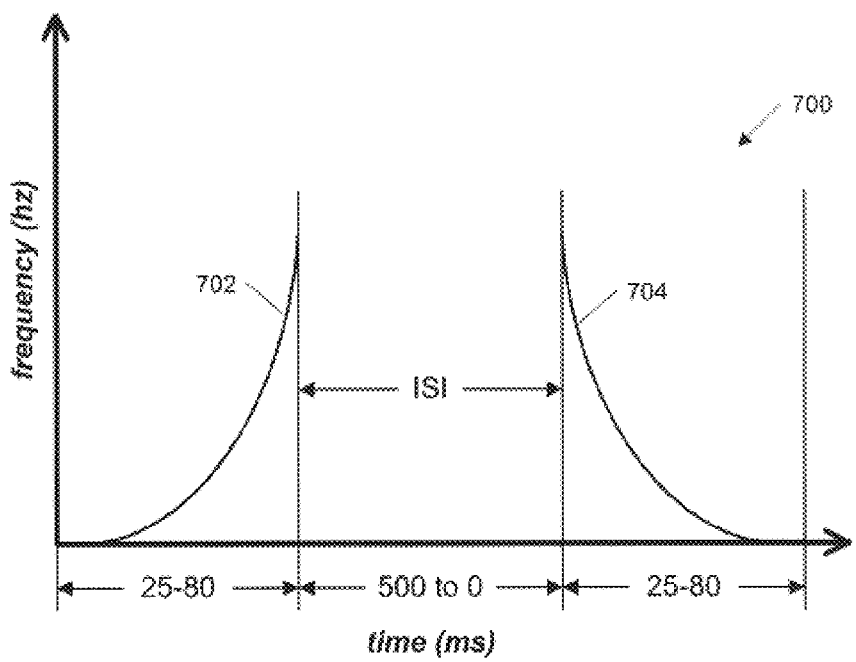
FIG. 7 is a chart illustrating an Inter-Stimulus-Interval (ISI) between two frequency sweeps.

A third method that may be used to train LLI subjects to distinguish short duration acoustic events is to provide frequency sweeps of varying duration, separated by a predetermined interval, as shown in FIG. 7. More specifically, an upward frequency sweep 702, and a downward frequency sweep 704 are shown, having duration's varying between 25 and 80 milliseconds, and separated by an inter-stimulus interval (ISI) of between 500 and 0 milliseconds. The duration and frequency of the sweeps, and the inter-stimulus interval between the sweeps are varied depending on the processing level of the LLI subject, as will be further described below.

Utilization of up-down frequency sweeps with varying ISI has been fully described in U.S. Pat. No. 5,813,862 entitled "METHOD AND DEVICE FOR ENHANCING THE RECOGNITION OF SPEECH AMONG SPEECH-IMPAIRED INDIVIDUALS", and is hereby incorporated by reference.

The above described methods have been combined in a unique fashion by the present invention to provide an adaptive training method and apparatus for training subjects having abnormal temporal processing abilities to recognize and distinguish short duration acoustic events that are common in speech. More specifically, emphasis has been used to intensify format transitions of stop consonants that are presented to a subject. It is believed that the differential gain of critical acoustic components generates more vigorous neural activity, which leads to better signal differentiation by neural networks involved in speech perception.

The present invention is embodied into a computer program entitled Fast ForWord II by Scientific Learning Corporation. The computer program is provided to an LLI subject via a CD-ROM that is input into a general purpose computer such as that described above with reference to FIG. 1. In addition, a user may log onto a server, via an Internet connection, for example, to upload test results, and to download training parameters for future exercises. Specifics of the present invention will now be described with reference to FIGS. 8–16.

Figure 8:
FIG. 8 is a screen shot of several games according to the present invention.

Referring first to FIG. 8, a pictorial representation is shown of a game selection screen 800. The game selection screen 800 is similar to that provided to a subject upon initialization of the computer program according to the present invention. The game selection screen 800 includes the titles of five computer games that provide distinct training exercises for improving language recognition in subjects who abnormally process temporal acoustic events, and for building, or rebuilding the neurological connections necessary to accurately process phonemes at the rates common in speech. The game titles include: 1) Start-Up Stories; 2) Polar Cop; 3) Trog Walkers; 4) Treasure in the Tomb; and 5) Bug-Out!.

When a subject begins execution of the Fast ForWord II computer program, s/he is presented with a screen similar to the screen 800. More specifically, upon initiation of the program, the subject is presented with a screen that lists the subjects that are currently being trained by the program. The subject, or instructor, then selects his/her name from the list. Once the subject has selected his/her name, a screen similar to 800 appears, typically listing the five programs, according to a training schedule that is dictated by the program, or is modified by an instructor. The order of the games that is presented in the screen 800 may vary from day to day, depending on which games the subject has previously played. In addition, after a subject has completed play of a particular game, that game may be shown "grayed out", indicating that it may not be selected again that day unless all other scheduled exercises have already been played. The subject then selects to play one of the games listed.

In one embodiment, a training schedule is provided by a certified Speech and Language Professional (SLP), and the SLP oversees each training session according to the schedule. An exemplary schedule requires a subject to cycle through the games for an hour and forty minutes, five days per week, for approximately six weeks.

In an alternative embodiment, the game schedule is specified by an SLP at a remote server, and the daily parameters of the schedule are downloaded to the subject's computer, either daily or weekly. The schedule can be optimized over the course of the training program according to the performance or skill of the subject. It can also be used to help manage time in each game so that all of the games are completed in about the same time at the end of the training program. This can be accomplished by an automated computer algorithm that adjusts the time allotted for each training exercise. This algorithm is individually adaptive and can adjust the times for each exercise on an individual subject basis using performance and estimates of time to complete the entire training sequence. This embodiment allows a subject to obtain the benefits of the Fast ForWord II program, and the oversight of a certified SLP, regardless of his/her geographic location. One skilled in the art will appreciate that the training schedule could either be provided in a window on the subject's computer, or could actually control the game selection screen to prompt the user only for those games required on a particular day.

Once a subject selects a particular game, s/he is taken into that particular game's module. Alternatively, once the subject selects his/her name from the list, the particular games may be presented, in a predefined order, without requiring the subject to first select the game.

The present application provides a detailed description of the game "Bug Out!". The other games shown in FIG. 8 are described in co-pending U.S. patent applications: SLC:810 (Polar Copy); SLC:811 (Trog Walkers); SLC:812 (Treasure in the Tomb); and SLC:814 (Start-Up Stories), which are hereby incorporated by reference.

Bug Out! is a game that adaptively trains a subject to distinguish between similarly sounding phonemes and to associate phonemes with their graphemes. Phonemes include words with three to five letters having consonant (C), consonant-vowel-consonant (CVC), and consonant-vowel-consonant—consonant (CVCC) constructs. The game presents a grid having matching pairs of phonemes (and associated graphemes). When a subject selects an element on the grid, its phoneme is presented aurally. In addition, its associated grapheme is presented. When the subject uncovers an element that corresponds to one previously heard/uncovered, the subject is to match the current element with the prior element. As the subject accurately identifies the previously selected elements with the current elements, the amount of processing applied to the phonemes is reduced, ultimately to the level of normal speech. The trials are placed within a game environment to entertain and amuse the subject so that multiple iterations are considered enjoyable rather than tedious. For purposes of the present invention, the terms "phoneme" and "word" are used interchangeably, to designate particular aural events that must be perceived by a subject.

The object of the Bug Out! game is to match pairs of sounds and their associated graphemes, and in so doing clear the playing field of tiles. Each of the tiles represent a phoneme/grapheme. When a tile is selected, its phoneme is played, and its grapheme is displayed. The tile remains uncovered illustrating its associated grapheme. As the subject uncovers tiles s/he will uncover tiles that match previously uncovered tiles. The subject then selects the matching tile to remove the pair from the playing field.

A complete description of the trial methodology used by Bug Out!, as well as the phonemes tested, and the adaptive nature of the game, will be provided below with reference to FIG. 16. However, to better appreciate the methodology used within Bug Out!, an overview of the game will first be provided, with reference to several screens within the game.

Figure 9:
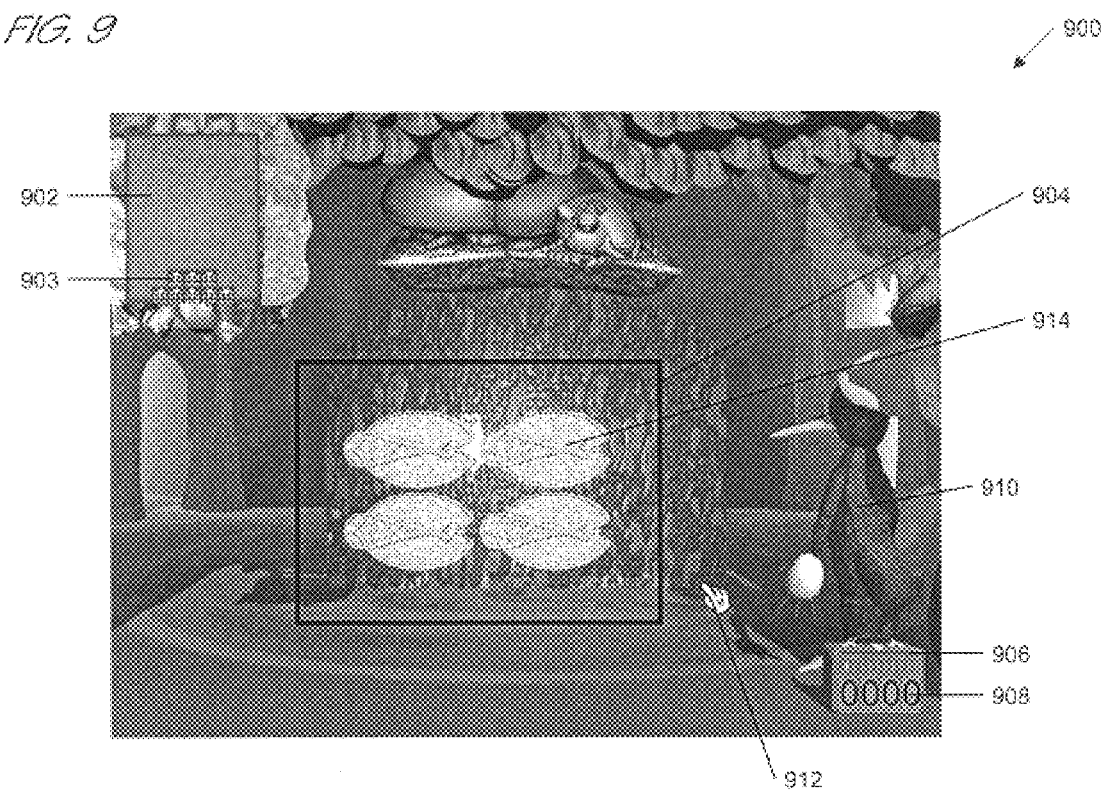
FIGS. 9–15 illustrate various screen shots during game play of a game called "Bug Out!" according to the present invention.

Referring to FIG. 9, a screen 900 is shown with a progress monitor 902, a tile area 904, a trial indicator 906, a score indicator 908, a platypus 910, and a selection hand 912.

At the beginning of each trial, the progress monitor 902 contains a number of blocks 903 that provide a visual indication of the number of guesses that are allowed for the subject to clear the tile area 904. For example, in the tile area 904, 4 tiles 914 are shown. Within the progress monitor 902, 8 blocks 903 are shown. Thus, the subject has 8 opportunities to pair the tiles 914, as will be further described below. If the subject does not clear the tile area 904 in 8 attempts, the trial is not successfully passed. However, if the subject clears the tile area 904 in 8 or less attempts, the subject's score is incremented according to the number of blocks 903 remaining in the progress monitor 902.

As mentioned above, the tile area 904 contains a number of tiles 914. In one embodiment, the number of tiles 914 within the tile area 904 are either 4, 8 or 16, although other combinations are possible. The number of tiles 914 within the tile area 904 vary according to the skill level obtained by the subject.

The trial indicator 906 indicates the number of successful trials completed by the subject. In one embodiment, the trial indicator 906 tracks from between 5 and 10 successfully completed trials, to mark the potential for transition to a secondary game play (further described below).

The score indicator 908 is used to provide feedback to the subject regarding his/her score within a game.

The platypus 910 is present in most of the game scenes to provide animations to reward and amuse the subject during game play.

The selection hand 912 is used to select a particular tile 914. More specifically, the subject moves a computer mouse (as described above with reference to FIG. 1), thereby moving the selection hand 912. When the selection hand is over one of the tiles 914, the subject presses a button on the mouse to cause selection of the tile.

Figure 10:
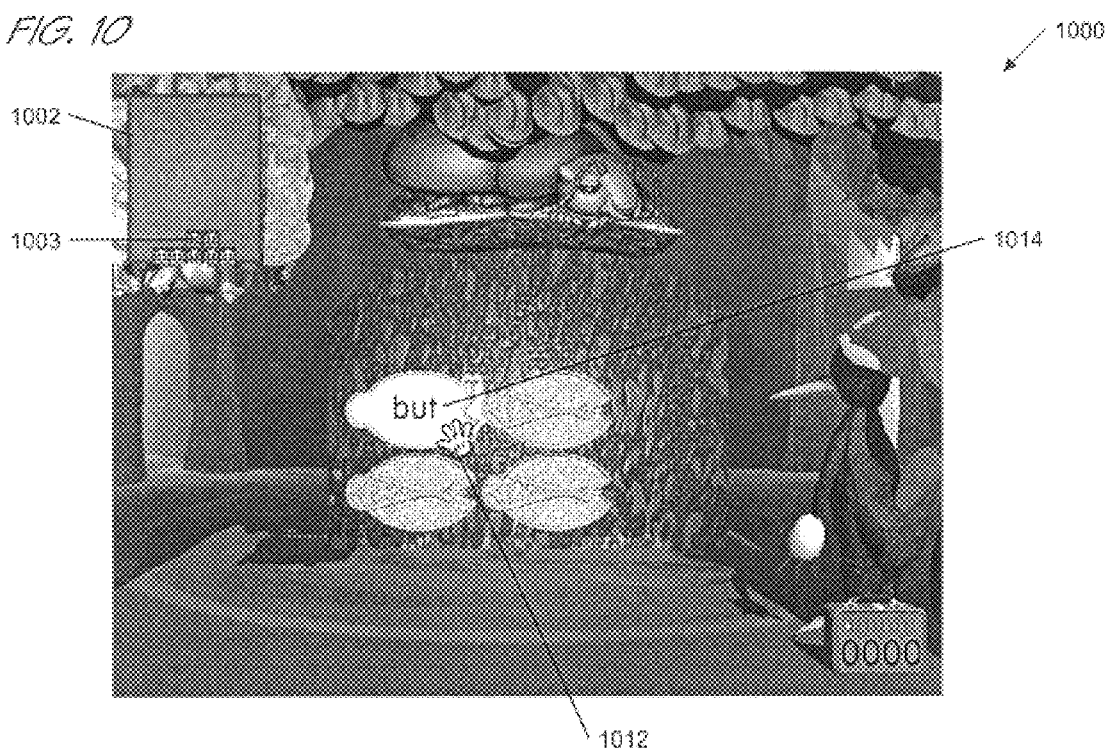

Referring now to FIG. 10, a game screen 1000 is shown. The game screen 1000 includes all of the elements described above with reference to FIG. 9. In addition, screen 1000 illustrates selection by the hand 1012 of one of the tiles 1014. When a subject selects the tile 1014, it turns into a grapheme that represents a phoneme from one of a plurality of stimulus sets. Simultaneous to the display of the grapheme 1014, its associated phoneme is played for the subject, either through speakers connected to a computer, or via headphones. Also, upon selection of the tile 1014 by the hand 1012, one of the blocks 1003 within the progress monitor 1002 is removed, thereby indicating to the subject that only 7 opportunities remain for the subject to pair the tiles.

Figure 11:
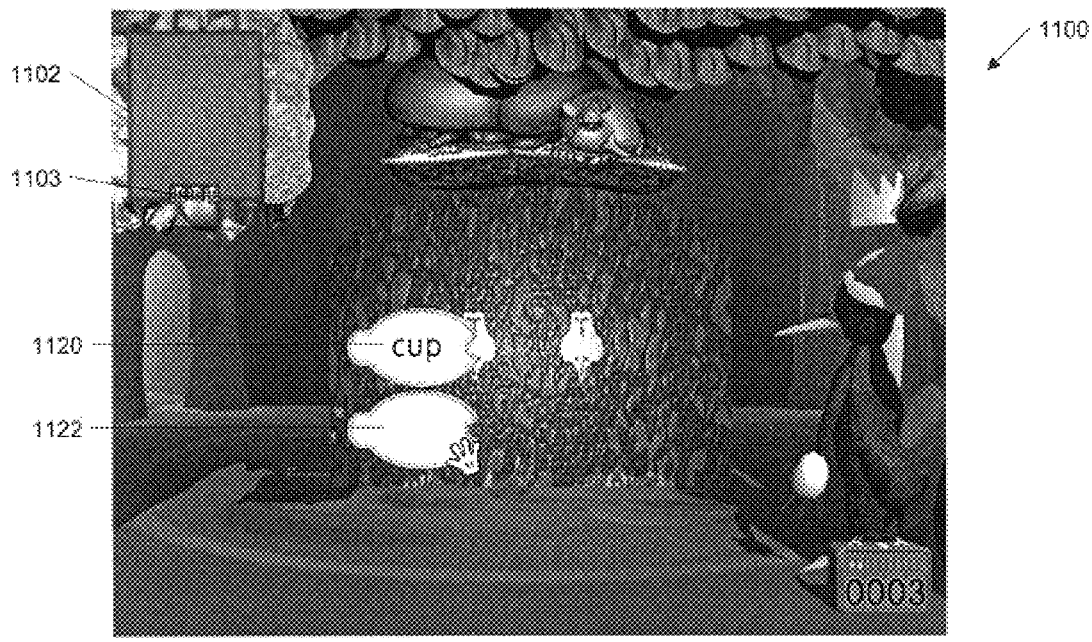

Referring now to FIG. 11, a screen 1100 is shown. The screen 1100 shows two remaining tiles 1120 and 1122. As mentioned above, every phoneme/grapheme is represented by a pair of tiles that must be matched by a subject. The first time a phoneme/grapheme is selected, a tile 1120 turns into an associated grapheme, and plays the phoneme. The tile 1120 remains uncovered to illustrate the grapheme, and the phoneme it represents. However, when a tile 1122 is selected that is associated with the second phoneme/grapheme of the pair, its phoneme is played, but the associated grapheme is hidden. That is, the subject is prevented from pairing tiles based solely on appearance. Rather, the subject must auditorily discern which tile the uncovered tile 1122 should be paired with. Upon hearing the phoneme presented with selection of tile 1122, the subject must then select the tile 1120, that is its match. When the two tiles 1122, 1120 are selected in sequence, the tile 1122 briefly displays its grapheme, and then the two tiles 1122, 1120 disappear from the screen 1100. In addition, each time the subject selects a tile, a block 1103 is removed from the progress monitor 1102. In screen 1100, the subject has just 3 more blocks 1103, indicating that s/he has only 3 more opportunities clear the screen 1100 of tiles.

Figure 12:
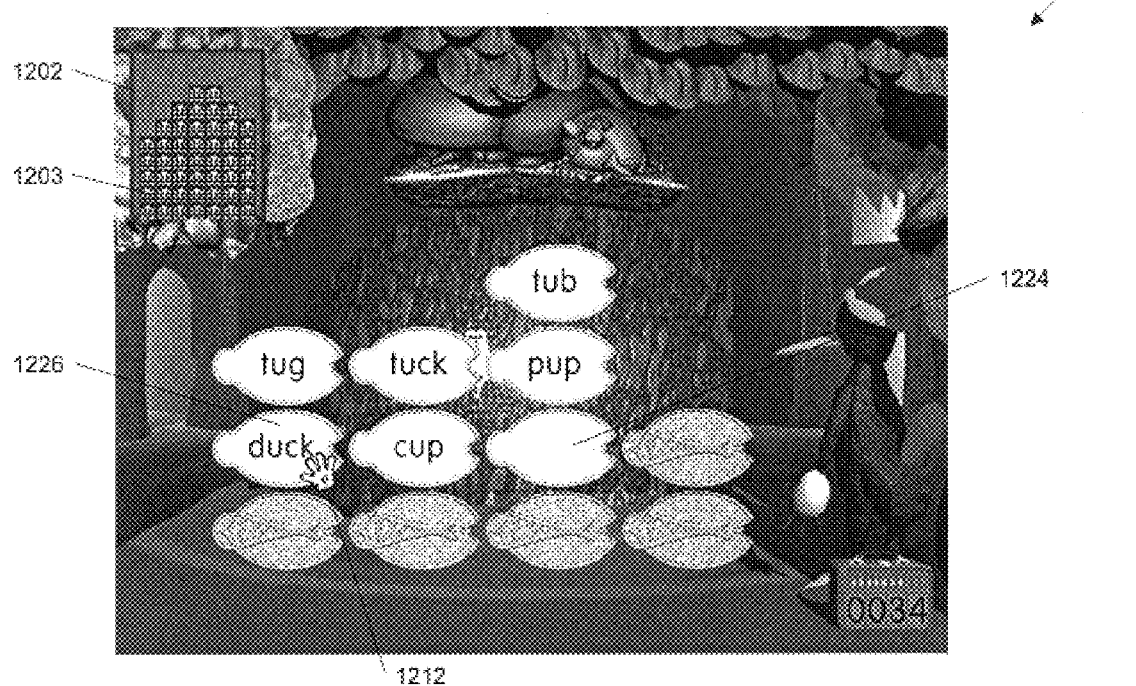

Referring now to FIG. 12, a screen 1200 is shown. The screen 1200 illustrates game play of a 4×4 grid (i.e., 16 tiles). In one embodiment, a subject is given 60 opportunities to pair eight pairs of tiles. The number of opportunities is shown by the number of blocks 1203 within the progress indicator 1202. In screen 1200, six distinct tiles have been uncovered by the subject that are illustrated by their graphemes. In addition, a tile 1224 is shown, without a grapheme. This indicates that its paired phoneme/grapheme has already been uncovered by the subject. As mentioned above, when the tile 1224 is uncovered, its associated phoneme is played. The subject must then select, based on his/her discrimination of the played phoneme, which of the uncovered tiles corresponds to the played phoneme. In screen 1200, the subject is shown selecting the tile 1226 with the hand 1212. If the subject correctly pairs the tile 1224 with the tile 1226, they will both be removed from the playing field. However, if the subject incorrectly pairs the tiles, that is, if the tile 1226 does not correspond with the tile 1224, both of the tiles will remain on the playing field.

Figure 13:
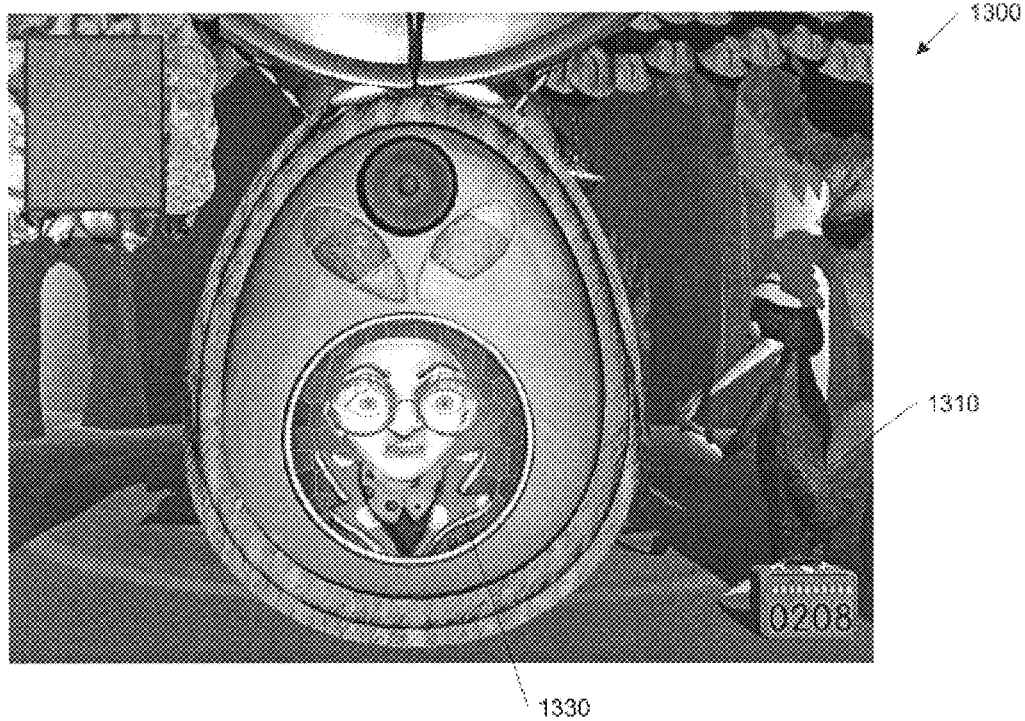

Referring now to FIG. 13, a screen 1300 is shown. The screen 1300 does not contain any of the aforementioned tiles. Rather, the screen 1300 includes a reward animation 1330 that contains encouraging and challenging dialog from a Dr. Trubug. The animations occur with successful and unsuccessful play, with the nature of the message determined by a trial outcome. Dr. Trubug 1330 often sends the platypus 1310 on particular errands or missions the provide interesting auditory effects. The number of successful/unsuccessful trials that are required to obtain a reward animation vary from 5 to 10.

Figure 14:
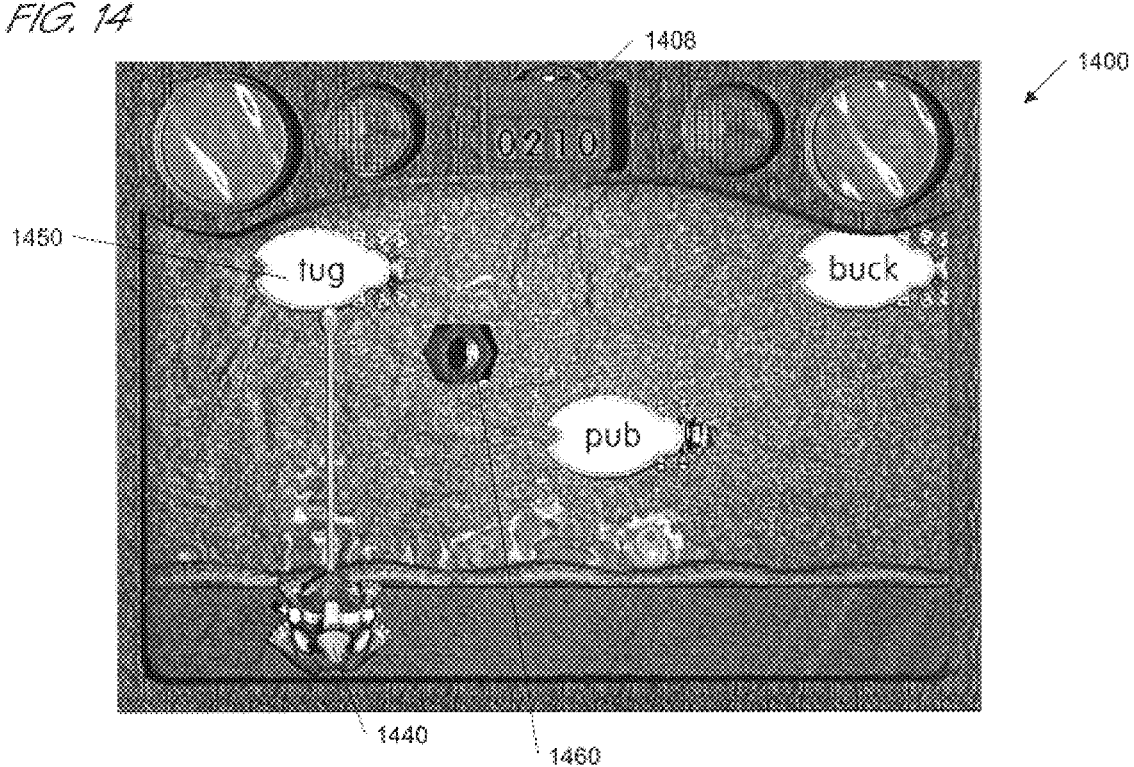

Referring now to FIG. 14, a screen 1400 is shown. The screen 1400 illustrates a reward game play (or secondary game play) after a subject has successfully completed a primary game play for a particular stimulus set. More specifically, after a subject completes 5 successful trials in the primary game play, they are transported to the screen 1400. The subject is then allowed 2 minutes within the secondary game play area. The object of this part of the game play is to strengthen the association of played phonemes with their grapheme in an entertaining arcade environment.

The screen 1400 includes a frog 1440 that is attempting to eat a bug 1450. Upon initiation of game play, a phoneme is aurally presented to the subject. After the phoneme is presented, a series of bugs 1450 begin crawling, from left to right, across the screen 1400. Each of the bugs 1450 contain a grapheme on their back, corresponding to the stimulus set that is currently being tested. One of the bugs 1450 will contain the grapheme corresponding to the played phoneme. When the bug 1450 corresponding to the played phoneme appears, the subject is to line up the frog 1440, and "shoot" the bug 1450. That is, when properly lined up with the appropriate grapheme, upon pressing of a mouse button by the subject, the frog 1440 will eat the bug 1450. Correct identification of the played phoneme will increase the subject's score, as shown by the score indicator 1408. In addition, as game play proceeds, a number of target phonemes (i.e., played phonemes), and foils (alternate phonemes within a stimulus set) may be presented. Moreover, to increase interest in secondary game play, a number of blockades 1460 appear which interfere with the subject's ability to successfully capture a target. As the subject's skill increases, the number of blockades 1460 also increases. After 2 minutes of secondary game play, the game returns to primary game play, as described above.

Figure 15:
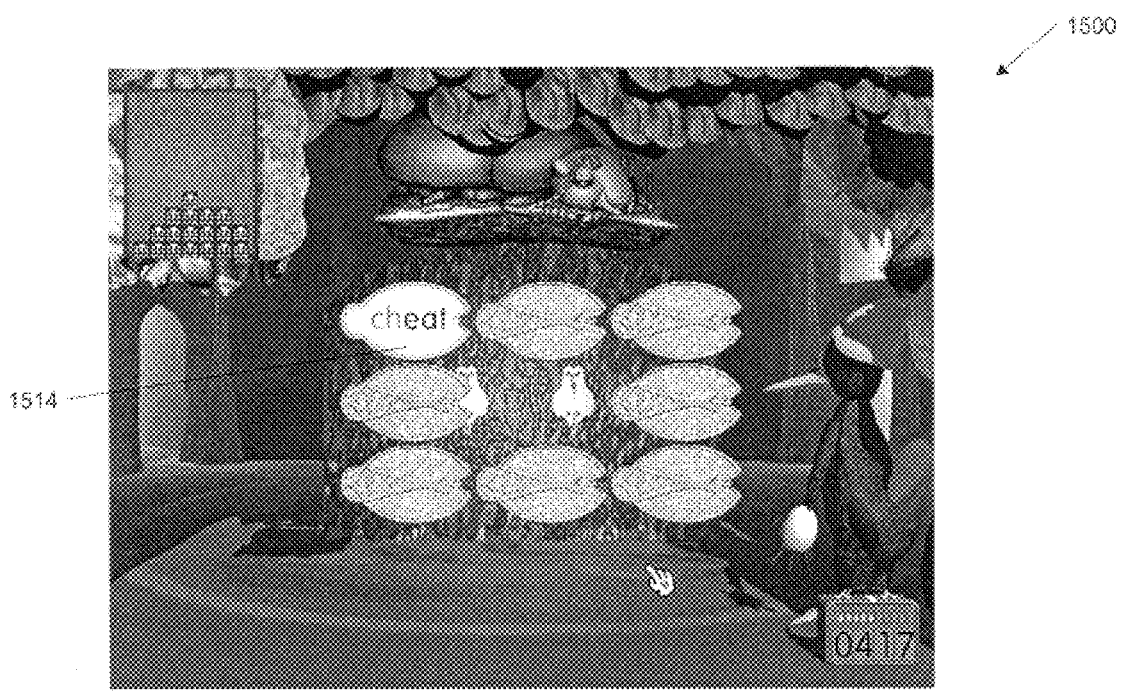

Referring now to FIG. 15, a screen 1500 is shown. The screen 1500 contains all of the elements described above with respect to FIG. 9. In addition, the tiles 1514 have graphemes with particular letters highlighted. In one embodiment, graphemes can highlight the particular consonant (C), or consonant—consonant (CC) construct that is being tested.

With the above overview of the Bug Out! game, a detailed description of the methodology, and adaptive controls of the game will now be provided.

Stimulus Sets

In one embodiment, Bug Out! provides trials to train a subject to distinguish between consonants using ordered sets called "stimulus sets". Each stimulus set provides a set of words that have the same vowel construct, but differ in consonant, either at the beginning of a word, or at the end of a word. For example, three words within stimulus set 1 are: kick, kid, and kit. In this example, the stimulus set uses consonant-vowel-consonant (CVC) words to train the subject to recognize the end consonants "ck", "d" and "t". Other stimulus sets are provided to test consonant discrimination in combination with other vowels, consonant discrimination at the end of words, and consonant discrimination in consonant-vowel-consonant—consonant (CVCC) words. A complete list of the stimulus sets used in Bug Out! is provided in Appendix A.

A stimulus set consists of pairs of matching words that form a grid. The grid pattern begins with a 2×2 grid (2 pairs of matching words) and progresses to a 3×3 grid (4 pairs of matching words) and finally to a 4×4 grid (8 pairs of matching words). The 3×3 grid eliminates 1 of the tiles in the set so that there are 8 tiles (4 pairs) in the 3×3 grid. Game play always begins on a 2×2 grid. Successful progress through the 2×2 grid level is accomplished when the tiles are cleared in 8 or fewer selections. Regardless of the grid structure, completion of a grid in the maximum number of selections, or less, is counted as a promotion, while completing it in more than the number allowed is a demotion. The relationship between the maximum number of selections, and the grid size is as follows:

| Grid Size: | 2 × 2 | 3 × 3 | 4 × 4 |
|---|---|---|---|
| Selections: | 8 | 19 | 60 |

Stimulus Stages

There are 10 stages of game play provided in Bug Out! The stages are:

| Stage | Grid Size |
|---|---|
| 1 | 2 × 2 |
| 2 | 2 × 2 |
| 3 | 2 × 2 |
| 4 | 3 × 3 |
| 5 | 3 × 3 |
| 6 | 3 × 3 |
| 7 | 4 × 4 |
| 8 | 4 × 4 |
| 9 | 4 × 4 |
| 10 | 4 × 4 |

Each day a subject plays the game Bug Out! s/he starts at stage 1. The subject remains at stage 1 until s/he successfully completes it, for a particular stimulus set, in less than or equal to the maximum number of allowed selections. The subject then progresses through each of the stages, for a particular stimulus set, just as with stage 1.

Stages 4 and 10 have special rules associated with them. Stage 4 is established as a "slipcat" round, meaning that if the subject demotes while in stage 4, s/he begins with a different stimulus set rather than reverting back to stage 3. It is believed that if the subject is having difficulty with the current stimulus set, they should attempt another stimulus set rather than demoting to the prior stage.

Stage 10 is termed the "decision" round. That is, if the subject successfully completes a decision round for a given stimulus set, at a given processing level, s/he will never encounter that stimulus set at that processing level again. Successfully completing the decision round takes the subject to another uncompleted stimulus set. If the subject does not successfully complete the decision round, s/he simply drops back to stage 9.

Speech Processing

For each trial presented to a subject, the words within the stimulus stages may be processed to enhance the subject's ability to distinguish the target word from the distractor words. In one embodiment, Bug Out! provides 3 levels of speech processing for the target consonant portion of the target and foil words. Level 1 provides 20 dB of emphasis, without any time domain expansion. Level 2 provides 10 dB of emphasis, without any time domain expansion. Level 3 provides 0 dB of emphasis, without any time domain expansion (i.e., normal speech).

The emphasis uses an algorithm that differentially amplifies and disambiguates faster phonetic elements in speech. "Fast elements" in speech are defined as those that occur in the 3–30 Hz range within an envelope of narrow-band speech channels of a rate changed speech signal. An emphasis algorithm for these fast elements was implemented using two methods: a filter-bank summation method and an overlap-add method based on a short-time Fourier transform. Both of these emphasis algorithms, as well as other speech processing methods are fully described in co-pending U.S. patent application Ser. No. 08/982,189 (Docket SLC:707A), filed Dec. 17, 1997, entitled "METHOD AND APPARATUS FOR TRAINING OF SENSORY AND PERCEPTUAL SYSTEMS IN LLI SUBJECTS".

Progression Through Stimulus Sets

The following rules govern a subject's progression through the various stimulus sets, and processing levels, provided in Bug Out!:

1. A subject can move from a lower processing level to a higher processing level, but never back down.
2. A subject can move up to the next processing level when a decision round for all of the stimulus sets have been successfully completed.
3. Once a subject successfully completes a decision round for a given stimulus set at a given processing level, s/he will never see that stimulus set, at that processing level, again.

Phoneme/Grapheme Presentation

Phonemes, and their associated graphemes are attached to tiles which a subject selects. The tiles exist in one of three states: 1) unselected; 2) selected with grapheme displayed; and 3) selected without grapheme displayed. When a tile is selected, its associated phoneme is played. In addition, if the phoneme has not yet been presented to the subject, its associated grapheme will be displayed on the tile. However, if the phoneme has been played, the grapheme will not be displayed on the tile until a match is made. If a match is made, the grapheme is briefly displayed before the matched tiles are cleared. This is particularly illustrated in FIGS. 11 and 12 described above.

Figure 16:
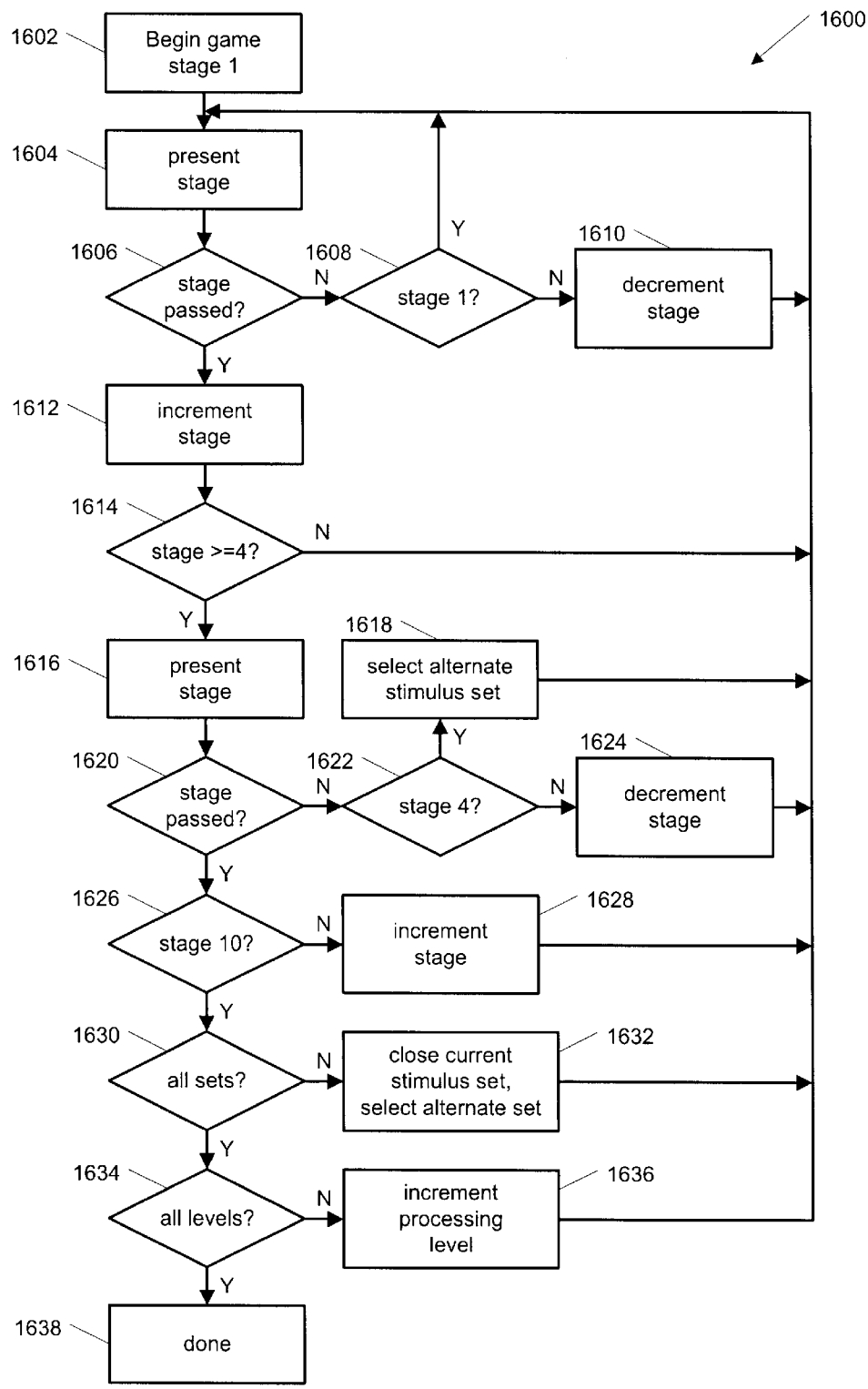
FIG. 16 is a flow chart illustrating progression through the game called "Bug Out!" according to the present invention.
Figure 17:
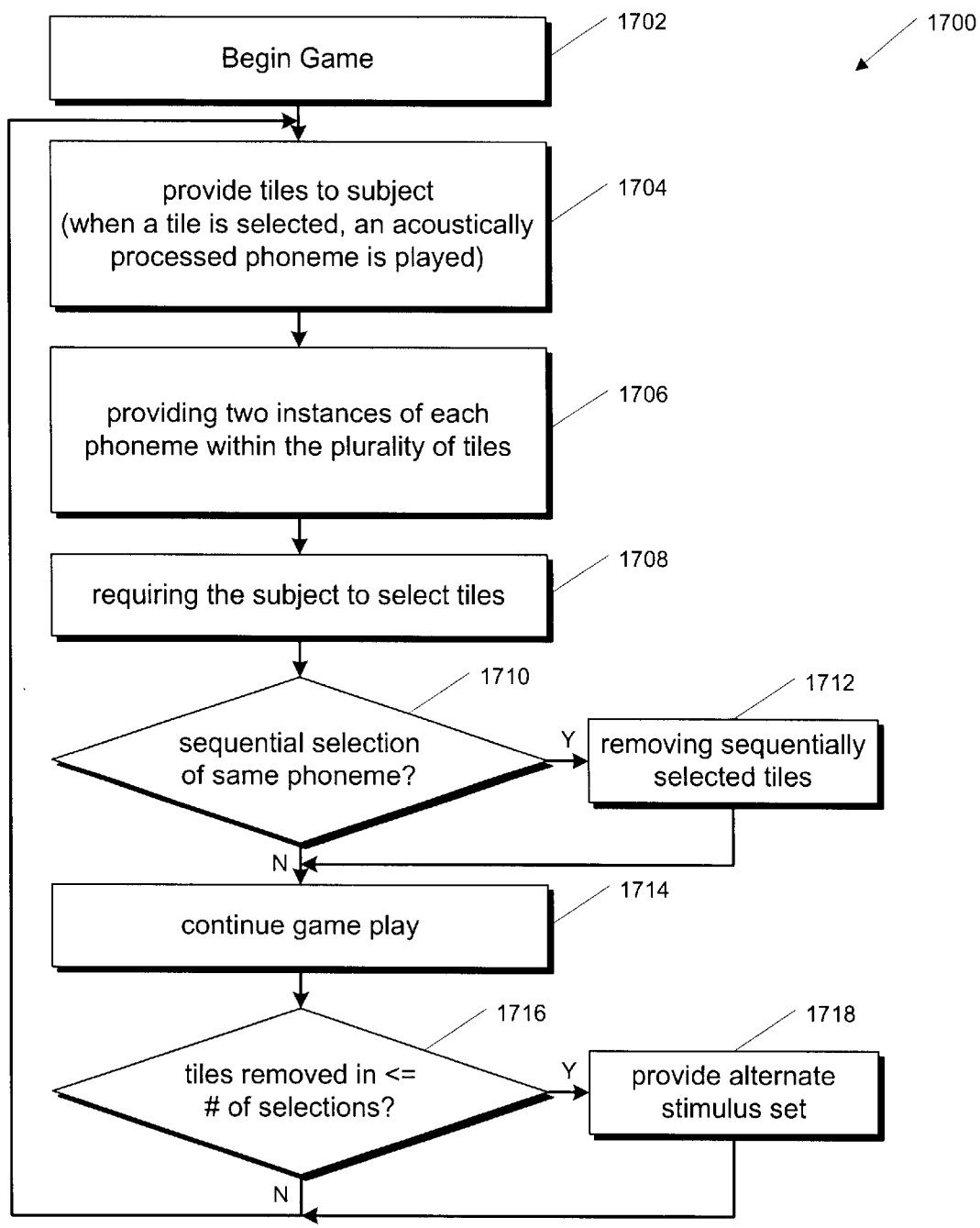
FIG. 17 is a flow chart illustrating progression through the game called "Bug Out!" according to the present invention.

Having provided a description of the stimulus sets used for training, of the stimulus stages that are created, and the speech processing used on the phonemes, a flow chart, as represented in FIG. 16, will now be described that illustrates the adaptive sequencing of Bug Out! thru all the sets, stages, and processing levels.

Referring to FIG. 16, a flow chart 1600 is shown illustrating the adaptive training methodology incorporated in the game Bug Out!. Game play begins at block 1602 where a first stimulus set is selected, and game play is reset to stage 1. The game then proceeds to block 1604.

At block 1604, a stage is presented to the subject. That is, a 2×2 grid of tiles is presented, as described above. The 2×2 grid of tiles contains two pairs of matched phonemes, along with their associated graphemes. Initially, the phonemes are presented at processing level 1, having 20 db of emphasis for the consonant portion of the phonemes. Flow then proceeds to decision block 1606.

At decision block 1606, a determination is made as to whether the subject has successfully passed the stage. As mentioned above, for a 2×2 grid, the subject is given eight selections to successfully match the paired phonemes/graphemes. If the subject matches the phonemes in eight or less selections, s/he progresses to block 1612. Otherwise, flow proceeds to decision block 1608.

At decision block 1608, a determination is made as to whether the current stage is stage 1. That is, is the subject currently being tested at the lowest stage in the game? If so, then game play remains at stage 1, using the current stimulus set, and flow proceeds back to block 1604. However, if the subject is currently being tested at a stage that is greater than stage 1, flow proceeds to block 1610.

At block 1610, the current stage is decremented. For example, if the current stage is stage 3, then the current stage is reset to stage 2. Flow then proceeds back to block 1604.

At block 1612, the current stage, for the current stimulus set, is incremented by 1. Flow then proceeds to decision block 1614.

At decision block 1614, a determination is made as to whether the current stage is greater than or equal to stage 4. As mentioned above, stage 4 is a "slipcat" round. If a subject progresses to stage 4 for a current stimulus set, s/he is prevented from reverting back to stages 1–3. If the current stage is not greater than or equal to 4, flow proceeds back to block 1604. Otherwise, flow proceeds to block 1616.

At block 1616, the current stage for the current stimulus set is presented to the subject. At this point, the subject has progressed to at least stage 4 for the current stimulus set. Flow then proceeds to decision block 1620.

At decision block 1620, a determination is made as to whether the subject has successfully completed the current stage for the current stimulus set. If so, then flow proceeds to decision block 1626. Otherwise flow proceeds to decision block 1622.

At decision block 1622, a determination is made as to whether the current stage is stage 4. If it is not stage 4, then flow proceeds to block 1624. However, if the current stage is stage 4, flow proceeds to block 1618.

At block 1618, the stage of the current stimulus set is recorded, the current stimulus set is left open for future trials, and an alternate stimulus set (if available), is selected for testing. Flow then proceeds to block 1604 for presentation of the new stimulus set.

At block 1624, the current stage is decremented. For example, if the current stage is stage 6, block 1624 decrements the current stage to be stage 5. Flow then proceeds to block 1604.

At decision block 1626, a determination is made as to whether the current stage is stage 10 (the last stage in the game). If not, flow proceeds to block 1628. Otherwise, flow proceeds to decision block 1630.

At block 1628, the current stage is incremented by one. Flow then proceeds back to block 1604.

At decision block 1630, a determination is made as to whether all stimulus sets have been successfully completed, through stage 10, for the current processing level. If not, then flow proceeds to block 1632. Otherwise, flow proceeds to decision block 1634.

At block 1632, the current stimulus set is closed. That is, the subject will not see the current stimulus set again, at the current processing level. Block 1632 then selects an alternate stimulus set for presentation. An alternate stimulus set includes any of the stimulus sets that have not been successfully completed, through stage 10, at the current processing level. Flow then proceeds to block 1604.

At decision block 1634, a determination is made as to whether all processing levels have been completed. If not, then flow proceeds to block 1636.

At block 1636, the current processing level is incremented. In one embodiment, there are three processing levels: 1) 20 db emphasis; 2) 10 db emphasis; and 3) 0 db emphasis (normal speech). Block 1636 increments the processing level, from level 1 to level 2, for example. Flow then proceeds to block 1604 to begin training of all of the stimulus sets, at the new processing level.

At decision block 1634, if a determination is made that the subject has completed all 10 stages, for all stimulus sets, at all processing levels, then flow proceeds to block 1638, where the game Bug Out! completes.

The flow chart 1600 thus describes a particular embodiment of the present invention for adaptively training a subject to distinguish between similar sounding words, and to associate particular words with their representative graphemes. While not specifically shown in FIG. 16, a reward play, as shown in FIG. 14, is provided to the subject after either a period of time, or a number of correct or incorrect trials.

Although the present invention and its objects, features, and advantages have been described in detail, other embodiments are encompassed by the invention. For example, the methodology of the present invention has been described with reference to a particular game entitled Bug Out! It should be appreciated that the story line for the game is inconsequential to the methodology used to train a subject in word/grapheme recognition. While the story line of the game should be engaging and entertaining, other story lines, game scenarios, etc., could be used.

In addition, a particular strategy has been shown in FIG. 16 for adaptively altering stimulus sets, stages, processing levels, etc., based on a subject's performance. Other performance criteria could be used to modify trial sequencing, without departing from the training methodology encompassed by the present invention.

Furthermore, the stimulus sets shown in Appendix A are not exhaustive. Rather, it is believed that they provide significant training for a subject, given particular time constraints on game play imposed by the market. However, additional or alternative stimulus sets are anticipated by the inventors.

Moreover, only 3 speech processing levels have been described for enhancing word recognition. It should be appreciated that additional or alternative speech processing could be used to further enhance a subject's neurological training. Such speech processing could include time expansion, as well as frequency component emphasis, of selected words, and could include varying the Inter-Stimulus-Interval between presented words.

Finally, the Bug Out! program has been shown for execution on a personal computer connected to a central server. However, as technology advances, it is envisioned that the program could be executed either by a diskless computer attached to a server, by a handheld processing device, such as a laptop, or eventually by a palmtop device such as a Nintendo GameBoy. As long as the graphical images and auditory prompts can be presented in a timely fashion, and with high quality, the nature of the device used to present the material is irrelevant.

Those skilled in the art should appreciate that they can readily use the disclosed conception and specific embodiments as a basis for designing or modifying other structures for carrying out the same purposes of the present invention without departing from the spirit and scope of the invention as defined by the appended claims.

APPENDIX A

GROUP 1

| Stim Set 1 | Stim Set 2 | Stim Set 3 |
|---|---|---|
| big | buck | back |
| bit | bud | bag |
| dig | but | bat |
| dip | cup | cab |
| kick | cut | cap |
| kid | duck | cat |
| kit | dug | gap |
| pick | pub | pack |
| pig | pup | pat |
| pit | tub | tack |
| tick | tuck | tag |
| tip | tug | tap |

GROUP 2

| Stim Set 4 | Stim Set 5 | Stim Set 6 | Stim Set 7 | Stim Set 8 |
|---|---|---|---|---|
| eat | ock | ake | air | ear |
| beat | block | bake | pair | dear |
| neat | hock | make | hair | gear |

APPENDIX A-continued

| seat | jock | sake | chair | fear |
|---|---|---|---|---|
| feat | lock | fake | stair | tear |
| heat | mock | take | dare | rear |
| peat | sock | lake | care | hear |
| pleat | tock | rake | mare | sear |
| cleat | rock | wake | rare | clear |
| wheat | clock | brake | share | shear |
| cheat | shock | shake | blare | spear |

GROUP 3

| Stim Set 9 | Stim Set 10 | Stim Set 11 |
|---|---|---|
| big | peg | luck |
| beg | pig | lock |
| bug | pug | lick |
| bag | pog | lack |
| bet | pot | puck |
| bit | pat | peck |
| bat | pet | pack |
| but | pit | pick |
| bed | pup | tack |
| bid | pop | tick |
| bad | pip | tuck |
| bud | pep | tock |

We claim:

1. A method for adaptively training a subject's working memory by presenting a plurality of tiles within a video game environment, the plurality of tiles playing a plurality of phonemes when selected, each of the plurality of tiles having a corresponding tile that plays the same auditory phoneme, the method comprising:

a) upon selection of a first one of the plurality of tiles, playing a first phoneme, and displaying the first phoneme's associated grapheme;

b) upon selection of a second one of the plurality of tiles, playing a second phoneme;

c) if the first and second phonemes are the same, and are selected sequentially, removing both the first and second one of the plurality of tiles without displaying the second phoneme's associated grapheme; and d) if the first and second phonemes are not the same, retaining both the first and second one of the plurality of tiles until they are selected sequentially.

2. The method for adaptively training a subject's working memory, as recited in claim 1 wherein the plurality of tiles are an even number of tiles, and wherein the plurality of phonemes are paired, such that each phoneme within the plurality of phonemes has a match.

3. The method for adaptively training a subject's working memory, as recited in claim 1 wherein the plurality of tiles are graphical buttons that, when selected, play one of the plurality of phonemes, and visually change to indicate that they have been selected.

4. The method for adaptively training a subject's working memory, as recited in claim 3 wherein when selected, the plurality of tiles change into a grapheme corresponding to the played phoneme.

5. The method for adaptively training a subject's working memory, as recited in claim 1 wherein the first phoneme is acoustically processed to better distinguish it from similar sounding phonemes.

6. The method for adaptively training a subject's working memory, as recited in claim 1 wherein each of the plurality of phonemes presented by the plurality of tiles correspond to a stimulus set.

7. The method for adaptively training a subject's working memory, as recited in claim 6 wherein the stimulus set comprises a plurality of similar sounding phonemes.

* * * * *